United States Patent
Bissinger et al.

[11] Patent Number: 6,001,096
[45] Date of Patent: Dec. 14, 1999

[54] INSTRUMENT FOR ENDOSCOPIC SURGERY

[75] Inventors: Günter Bissinger, Teningen; Bernhard Hug; Clemens Scholz, both of Freiburg; Andrea Scarfi, Ostfildern-Ruit, all of Germany

[73] Assignees: Huttinger Medizintechnik GmbH; Gunter Bissinger Medizintechnik GmbH, both of Germany

[21] Appl. No.: 09/003,564

[22] Filed: Jan. 6, 1998

[30] Foreign Application Priority Data

Jan. 10, 1997 [DE] Germany ............... 197 00 605

[51] Int. Cl.⁶ ................................... A61B 17/39
[52] U.S. Cl. .................. 606/50; 606/46; 606/51; 606/170; 606/174
[58] Field of Search .................. 606/45, 46, 48–52, 606/170, 174, 206, 208

[56] References Cited

U.S. PATENT DOCUMENTS

| | | | |
|---|---|---|---|
| 5,258,006 | 11/1993 | Rydell et al. | 606/52 |
| 5,330,471 | 7/1994 | Eggers . | |
| 5,334,198 | 8/1994 | Hart et al. . | |
| 5,486,185 | 1/1996 | Freitas et al. | 606/206 |
| 5,827,281 | 10/1998 | Levin | 606/51 |

FOREIGN PATENT DOCUMENTS

| | | |
|---|---|---|
| 0 598 348 A1 | 5/1994 | European Pat. Off. . |
| 0 717 966 A1 | 6/1996 | European Pat. Off. . |
| 44 21 822 C1 | 10/1995 | Germany . |

*Primary Examiner*—Lee Cohen
*Attorney, Agent, or Firm*—Pendorf & Cutliff

[57] ABSTRACT

The invention is related to an instrument for endoscopic surgery. The instrument comprises a casing 10, further comprises a sliding tube 16 which extends into the casing with its proximal end 20 and which is disposed longitudinally slidable with respect to the casing by means of an actuating mechanism 38, further comprises an electrode tube 18 which extends through the sliding tube 16, which extends into the casing with its proximal end and is axially lockable therein, and further comprises two isolated wire pieces 32 which extend through the inside of the electrode tube 18. The wire pieces 32 which are adapted to be subjected to a high frequency current comprise branches 30 which protrude over the electrode tube 18 and the sliding tube 16 at their distal end, which are spread apart from one another slanted in opposite directions, which are elastically bendable with respect to each other in a radial direction against a spring force acting in the direction of spreading during a movement of the sliding tube 16, and which carry isolated bending sections 48 and, at their free ends, metallic electrodes 56. In order to be able to mechanically cut as well as coagulate, in a bipolar manner, biological tissue with the instrument, it is proposed according to the invention that the electrodes 56 are formed to be cutting blades having cutting edges 54, which are adapted to be moved with respect to each other in a scissor-like fashion under the action of the sliding tube 16 on the bending sections 48.

12 Claims, 4 Drawing Sheets

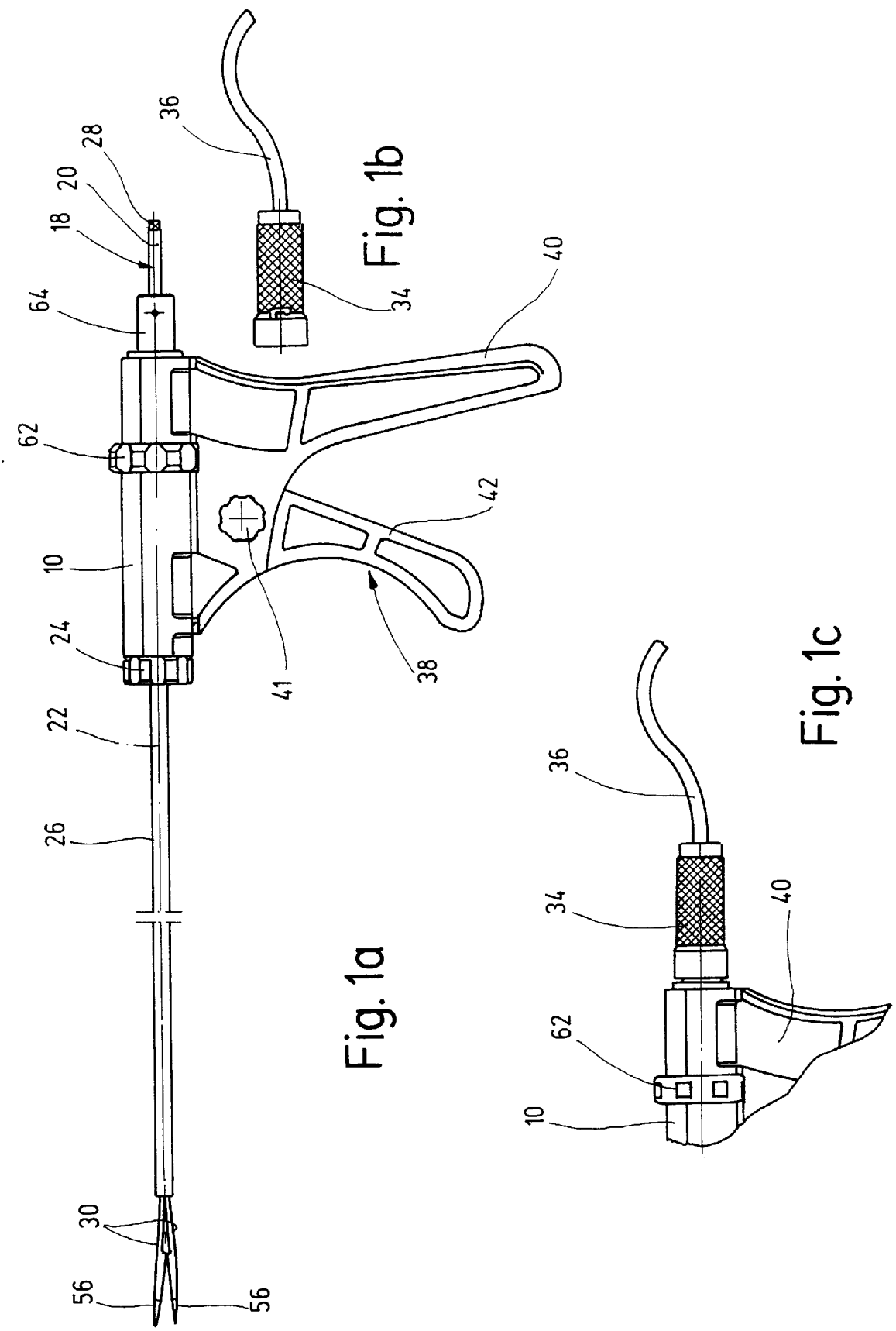

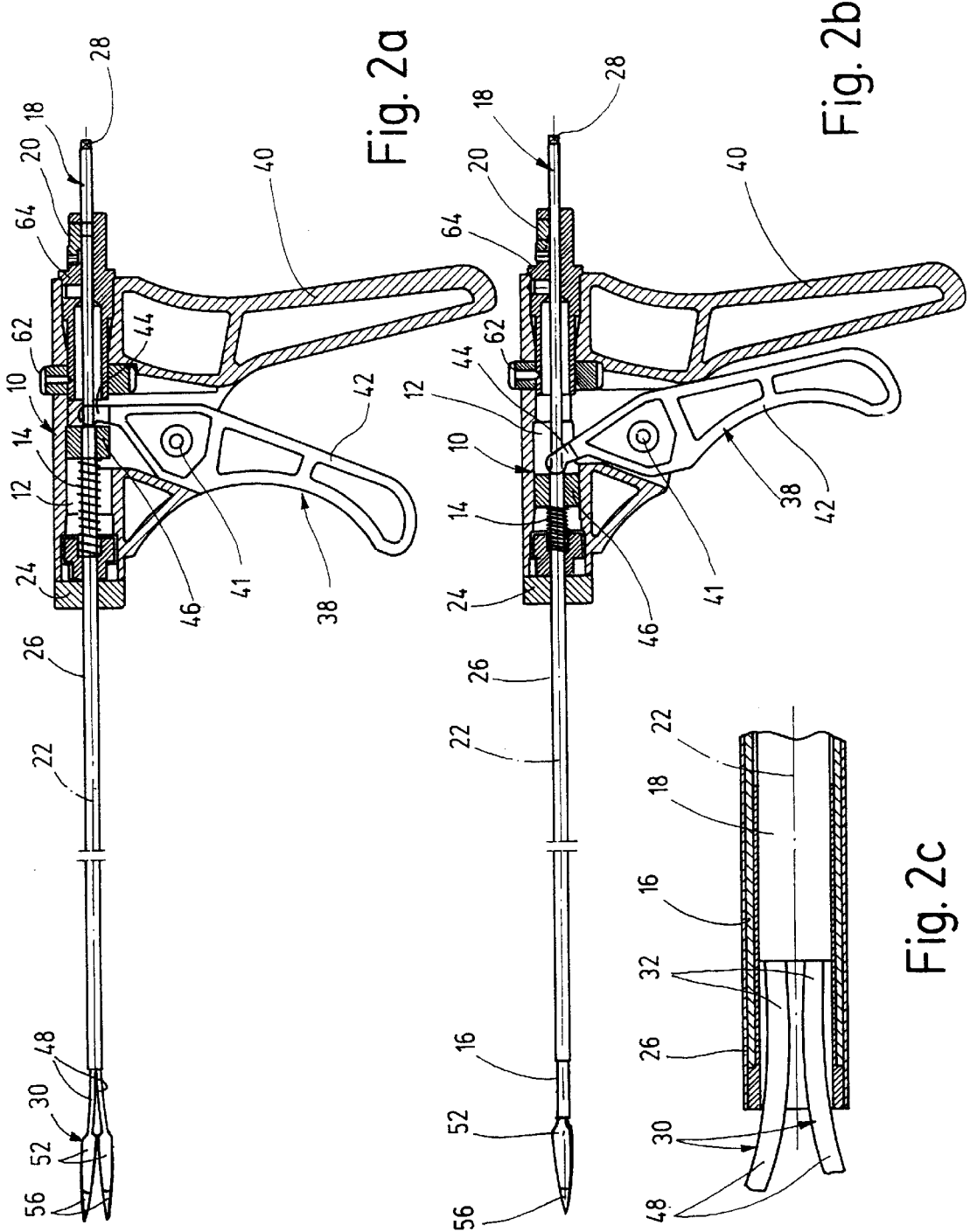

INSTRUMENT FOR ENDOSCOPIC SURGERY

BACKGROUND OF THE INVENTION

The invention is related to an instrument for endoscopic surgery, comprising a casing, further comprising a sliding tube which extends into the casing with its proximal end and which is disposed longitudinally slidable with respect to the casing by means of an actuating mechanism, further comprising an electrode tube which extends through the sliding tube, which extends into the casing with its proximal end and is axially lockable therein, and further comprising two isolated wire pieces which extend through the inside of the electrode tube, the wire pieces comprising branches which protrude over the electrode tube and the sliding tube at their distal end, which are spread apart from one another slanted in opposite directions, which are elastically bendable with respect to each other in a radial direction against a spring force acting in the direction of spreading during a movement of the sliding tube, and which carry isolated bending sections and, at their free ends, metallic electrodes, and which wire pieces comprise contact elements which are electrically connected to the electrodes at the proximal end and which are adapted to be connected to a high frequency power supply.

Instruments for endoscopic surgery of this type are known (DE-A-43 37 590), which are suited to coagulate and dissect tissue, and which to this end have an exchangeable electrode tube which is rotatable within the casing, the branches of which electrode tube are fit ted, for example, with hook-shaped, parallel electrodes. This makes it possible to first load the biological tissue onto the concave side of the hooks and to lift it up, and to then coagulate or dissect the tissue. With the convex side of the hook-shaped electrodes it is possible to run along a portion of tissue in a curve and to thereby coagulate or dissect the tissue by evaporation. In the course of this process, the distance between the two electrodes may be adjusted as seen necessary. By opening and closing the hook-shaped electrodes it is possible to dissect bluntly with or without current.

In minimal invasive surgery it often occurs that tissue has to be dissected. When using the bipolar coagulation pliers, the dissection is effected by a heating process which leads to an evaporation of tissue. In this, it is found to be disadvantageous that smoke is created by the heating and that the tissue is cauterized. Scissors are therefore often used for the dissection, which cut the tissue mechanically. In this, there is the danger of bleeding, though. In order to stop the bleeding bi-polarly the instrument has to be changed or a further instrument for coagulation has to be introduced.

OBJECTS AND SUMMARY OF THE INVENTION

Based on this, it is the object of the invention, to develop an instrument of the type described above, which can dissect mechanically as well as coagulate bi-polarly.

For the solution of this object the combination of features stated in patent claim 1 is proposed. Advantageous modifications and refinements of the invention result from the dependent claims.

The solution according to the invention is based on the idea that the electrodes are formed to be cutting blades having overlapping cutting edges, which are adapted to be moved with respect to each other in a scissor-like fashion under the action of the sliding tube on the bending sections. In order to be able to use the cutting blades for bipolar coagulation of biological tissue, the cutting blades are electrically isolated with respect to each other at least in their spread-apart state, whereas they may be electrically short-circuited in their cutting position by way of their touching cutting edges. The HF-power supply should therefore preferably be resistant to short circuits.

According to a preferred modification of the invention it is provided that the branches lie against each other at least partially overlapping in a scissor-like fashion in a transition section located between the cutting blades and the bending sections and are electrically isolated from each other at least in the region of overlap. In order to ensure a dependable mutual guidance of the cutting blades, the branches should be designed to resist bending in the transition sections.

According to an especially simple alternative of the invention, the transition sections are loosely pivotal with respect to each other. An improvement of the cutting action and of the mutual guidance of the cutting blades is attained according to a second alternative modification of the invention in that the transition sections are pivotally connected to each other by means of a transversely positioned, electrically isolated pivot pin. In order to avoid undesired short circuits, it is of advantage when the branches are enclosed and insulated from each other in the region of their bending sections and transition sections by an insulating layer which is open toward the cutting blades.

In order to cover the movement of the sliding tube toward the outside, it is of advantage when the sliding tube is guided within an outer tube which is solidly connected to the casing and that the sliding tube is movable with respect to the outer tube against the restoring force of a spring. In order to make adjusting the angle of the instrument at the site of surgery easier, the electrode tube may be adapted to be connected to the casing such that it is rotatable about its longitudinal axis.

With the instrument according to the invention it is possible to operate as follows:

The tissue to be treated is first laid open by inserting the closed or partially closed cutting blades into the tissue (without flow of current) and then spreading them open.

The tissue may be cut mechanically by the cutting blades without current.

The tissue to be treated can be coagulated under current before or after a cut or a spreading with opened cutting blades. The cutting blades are to this end pressed bluntly or flat against the tissue.

As far as the cutting blades are isolated with respect to each other in their closed or partially closed state, which may be attained by insulating layers, a continuous coagulation can take place during mechanical cutting.

BRIEF DESCRIPTION OF THE DRAWINGS

In the following, the invention is further described with reference to embodiments schematically shown in the drawing, in which:

FIG. 1a shows a side view of an electro-surgical instrument for bipolar coagulation and tissue dissection;

FIG. 1b shows a side view of a coupling device with a cable socket for the power supply;

FIG. 1c shows a detail of FIG. 1a with the coupling device being attached;

FIG. 2a and b show a longitudinal section through the instrument according to FIG. 1a in two actuating positions;

FIG. 2c shows a detail C of FIG. 2a in an enlarged, cut illustration;

DETAILED DESCRIPTION OF THE INVENTION

Figure 3A:
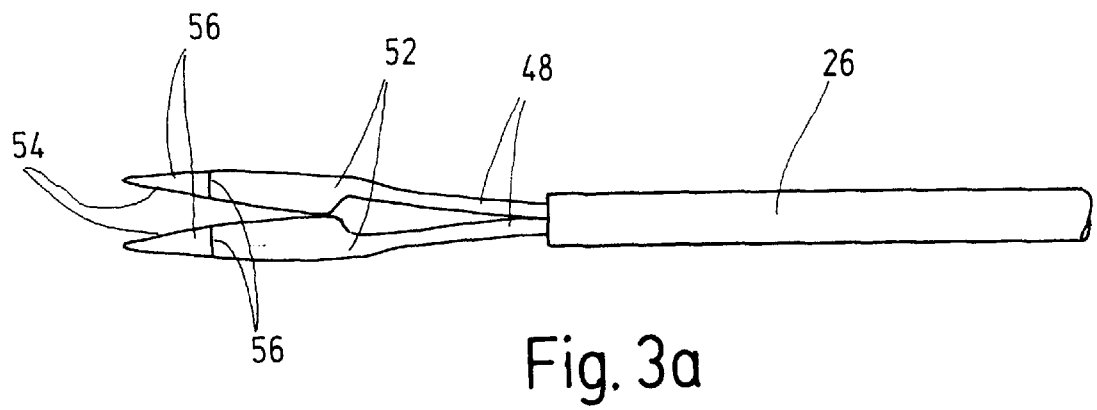
FIG. 3a to c show the distal end of the instrument according to FIG. 1a having a bipolar cutting insert without pivot pin in plan view with opened and closed cutting blades as well as in a side view.

The electro-surgical instrument shown in the drawing consists essentially of an instrument casing 10, a sliding tube 16 which engages with its proximal end an axial recess 12 of the casing 10 and which is movable with respect to the recess 12 against the force of a spring 14, an electrode tube 18 which can be inserted through the sliding tube 16 and which can be axially locked within the casing 10 with its proximal end 20, an outer tube 26 which protrudes unmovably over the casing 10, which can be removably connected to the casing 10 by means of the knurled nut 24, and which encompasses the sliding tube 16, two insulated pieces of wire 32 which are led through the electrode tube 18, which can be subjected to a high frequency current at contact elements 28 in the proximal region 20, and which are fitted with two elastically spreadable branches 30 at their distal end, as well as a coupling device 34 for the connection to a HF-power supply by means of a cable 36. The electrode tube 18 is designed to be an exchangeable electrode. It extends with its proximal end 20 through a sleeve 64 which is disposed in the casing 10 such that it cannot be moved linearly but rotated about the axis 22 by means of the knurled wheel 62, and is lockable in the sleeve 64 such that it cannot be displaced or rotated.

The instrument 10 has an actuating mechanism 38 which consists of a casing-fixed actuating leg 40 and an actuating leg 42 which may be pivoted with respect to the casing 10 about a transverse axis 41 and which extends into the casing 10 with a lever arm 44 and lies there against rear side of a stop member 46 which is disposed at the proximal end of the sliding tube 16.

Figure 3B:
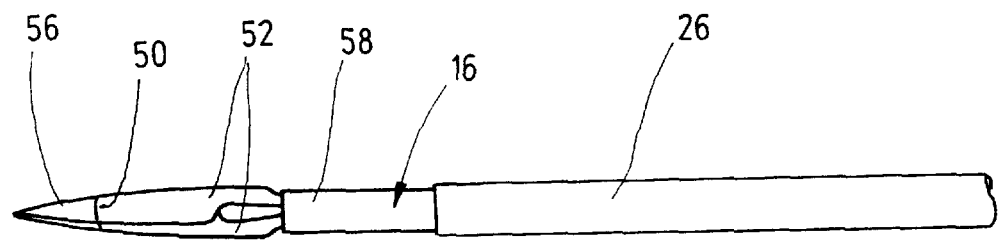
Figure 3C:
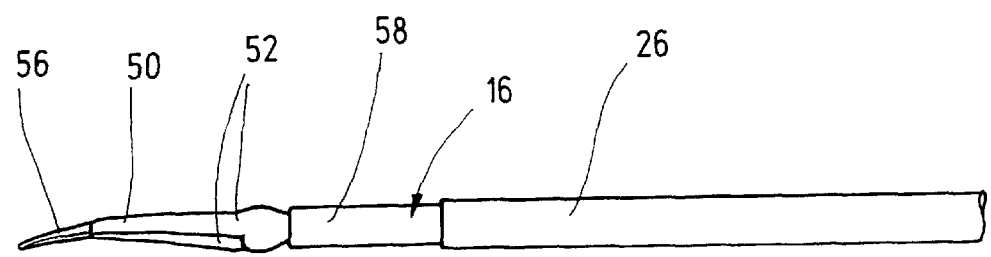
Figure 4A:
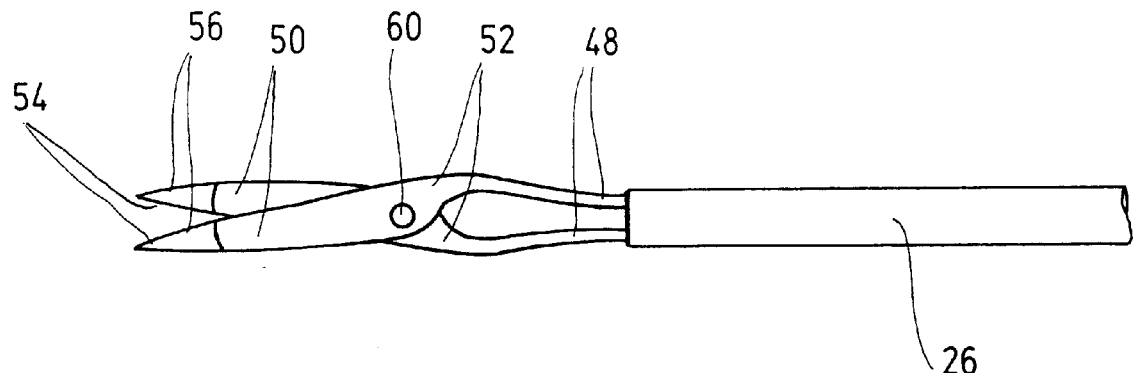
FIG. 4a to c show the distal end of the instrument according to FIG. 1a having a bipolar cutting insert with pivot pin in a plan view with opened and closed cutting blades as well as in a side view.
Figure 4B:
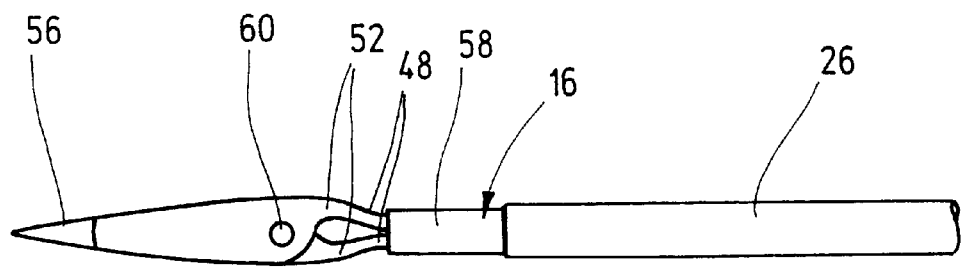
Figure 4C:
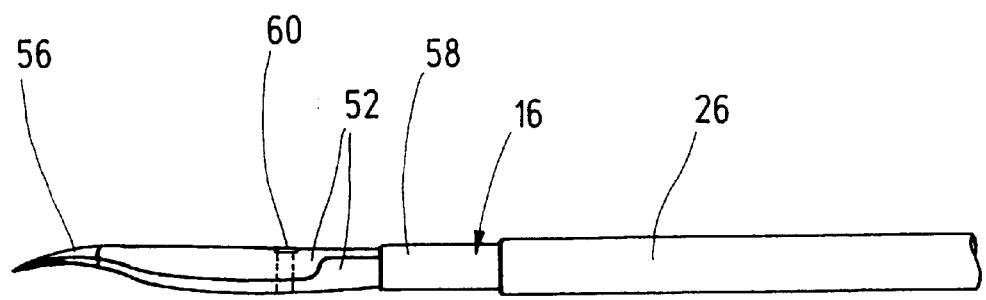

The branches 30 comprise elastically bendable bending sections 48 which protrude beyond the electrode tube 18 and which are spread apart at an angle in opposite directions, unbendable transition sections 52 which follow the bending sections and which are provided with an insulating covering 50 together with the bending sections, as well as metallic electrodes 56 following the transition sections, which electrodes 56 form the distal end and are at the same time formed to be cutting blades having a cutting edge 54, and which are electrically connected to the contact elements 28 for the HF power supply by means of the wire pieces 32. As can be seen from FIGS. 3c and 4c, the cutting blades 56 are curved in the same direction toward one side in the longitudinal direction. They may also be straight or bent, though. When pivoting the actuating leg 42 from its starting position shown in FIG. 2a into its end position according to FIG. 2b, the sliding tube 16 is displaced against the force of the thrust spring 14 such that the distal end 58 of the sliding tube 16 slides onto the bending sections 48 of the branches 30 and radially bends these elastically inwards from their spread-apart starting position according to FIGS. 2a, 3a, and 4a. At the same time the transition sections 52 and the cutting blades 56 are pivoted relative to one another in a scissor-like fashion, wherein the cutting edges 54 cross each other. In the embodiments according to FIGS. 1 to 3, the branches 30 together with their bending sections 48, transition sections 52 and cutting blades 56 are formed to have one arm, while in the embodiment according to FIGS. 4a to c they are formed to have two arms by virtue of the additional pivot pin 60 which penetrates the branches in the region of the transition sections 52 in an isolated fashion.

In summary the following is to be stated: The invention is related to an instrument for endoscopic surgery. The instrument comprises a casing 10, further comprises a sliding tube 16 which extends into the casing with its proximal end 20 and which is disposed longitudinally slidable with respect to the casing by means of an actuating mechanism 38, further comprises an electrode tube 18 which extends through the sliding tube 16, which extends into the casing with its proximal end and is axially lockable therein, and further comprises two isolated wire pieces 32 which extend through the inside of the electrode tube 18. The wire pieces 32 which are adapted to be subjected to a high frequency current comprise branches 30 which protrude over the electrode tube 18 and the sliding tube 16 at their distal end, which are spread apart from one another slanted in opposite directions, which are elastically bendable with respect to each other in a radial direction against a spring force acting in the direction of spreading during a movement of the sliding tube 16, and which carry isolated bending sections 48 and, at their free ends, metallic electrodes 56. In order to be able to mechanically cut as well as coagulate, in a bipolar manner, biological tissue with the instrument, it is proposed according to the invention that the electrodes 56 are formed to be cutting blades having cutting edges 54, which are adapted to be moved with respect to each other in a scissor-like fashion under the action of the sliding tube 16 on the bending sections 48.

We claim:

1. An instrument for endoscopic surgery, comprising:
   a casing having proximal and distal ends,
   a sliding tube having proximal and distal ends, which extends into the casing with its proximal end side and which is disposed longitudinally slidable between an extended and a retracted position with respect to the casing,
   an actuating mechanism operably engaging said sliding tube for sliding said sliding tube between said extended and retracted positions,
   an electrode tube having proximal and distal ends, which extends through the sliding tube and into the casing and at its proximal end region is axially lockable with respect to said casing, and
   two insulated wire pieces having proximal and distal ends, which wire pieces extend through the inside of the electrode tube, the wire pieces at their distal ends being fitted with branches of which the distal ends protrude beyond the electrode tube distal end and the sliding tube distal end, which protruding branches are spread apart from one another slanted in diverging directions, which branches are elastically bendable with respect to each other in a radial direction against a spring force acting in the direction of spreading during a movement of the sliding tube, and which comprise insulated bending sections and, at the distal ends of the bending sections, metallic electrodes, and which wire pieces at their proximal ends comprise contact elements which are electrically connected to said electrodes and which contact elements are adapted to be connected to a high frequency power supply,
   wherein said electrodes are formed as cutting blades having cutting edges, which are adapted to be moved with respect to each other in a scissor-like fashion under the action of the sliding tube on said bending sections.

2. The instrument of claim 1, wherein said cutting blades are electrically isolated with respect to each other at least in their spread-apart state.

3. The instrument of claim 1, wherein said cutting blades are electrically short-circuited in their cutting position by their touching cutting edges.

4. The instrument of claim 1, wherein the branches lie against each other at least partially overlapping in a scissor-like fashion in a transition section located between the cutting blades and the bending sections and are electrically insulated from each other at least in the region of overlap.

5. The instrument of claim 4, wherein the branches are enclosed and insulated from each other in the region of their bending sections and transition sections by an insulating layer which is open toward the cutting blades.

6. The instrument of claim 4, wherein said branches are designed to resist bending in said transition sections.

7. The instrument of claim 4, wherein said transition sections are loosely pivotal with respect to each other.

8. The instrument of claim 4, wherein the transition sections are pivotally connected to each other by means of a transversely positioned, electrically insulated pivot pin.

9. The instrument of claim 1, further comprising an outer tube solidly connected to said casing, wherein said sliding tube is guided within said outer tube between an actuated and a rest position, said instrument further comprising a spring operably engaging said sliding tube for biasing said sliding tube towards said retracted position, and said sliding tube being movable with respect to the outer tube against the restoring force of said spring.

10. The instrument of claim 1, wherein said electrode tube is adapted to be connected to the casing such that it is rotatable about its longitudinal axis.

11. The instrument of claim 9, wherein said outer tube is releasably connected to the casing.

12. The instrument of claim 1, wherein said cutting blades are curved or bent toward the same side, as seen in a longitudinal direction.

* * * * *